(12) United States Patent
May et al.

(10) Patent No.: US 11,109,895 B2
(45) Date of Patent: Sep. 7, 2021

(54) SPINAL CONSTRUCT

(71) Applicant: Warsaw Orthopedic, Inc, Warsaw, IN (US)

(72) Inventors: Jason M. May, Collierville, TN (US); William A. Rezach, Covington, TN (US); Lawrence G. Lenke, New York, NY (US); Roger P. Jackson, Prairie Village, KS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 247 days.

(21) Appl. No.: 15/334,873

(22) Filed: Oct. 26, 2016

(65) Prior Publication Data

US 2018/0110548 A1 Apr. 26, 2018

(51) Int. Cl.
*A61B 17/70* (2006.01)

(52) U.S. Cl.
CPC .................. *A61B 17/7037* (2013.01)

(58) Field of Classification Search
CPC ............ A61B 17/7032; A61B 17/7034; A61B 17/7035; A61B 17/7037; A61B 17/7046; A61B 17/7007; A61B 17/7008; A61B 17/7011; A61B 17/7041; A61B 17/7043; A61B 17/7049; A61B 17/705; A61B 17/7052
See application file for complete search history.

(56) References Cited

U.S. PATENT DOCUMENTS

| | | | |
|---|---|---|---|
| 5,885,286 A | 3/1999 | Sherman et al. | |
| 6,022,350 A * | 2/2000 | Ganem | A61B 17/7059 606/272 |
| 6,063,090 A * | 5/2000 | Schlapfer | A61B 17/7037 606/270 |
| 6,565,566 B1 | 5/2003 | Wagner et al. | |
| 8,021,397 B2 * | 9/2011 | Farris | A61B 17/7037 606/266 |
| 8,034,089 B2 | 10/2011 | Matthis et al. | |
| 8,097,025 B2 | 1/2012 | Hawkes et al. | |
| 8,167,025 B2 | 5/2012 | Rombs et al. | |
| 8,197,518 B2 | 6/2012 | Hammill et al. | |
| 8,197,910 B2 | 6/2012 | Chen et al. | |
| 8,298,265 B2 | 10/2012 | Purcell et al. | |
| 8,298,275 B2 | 10/2012 | Rezach | |
| 8,556,938 B2 * | 10/2013 | Jackson | A61B 17/7008 606/269 |
| 8,998,959 B2 * | 4/2015 | Jackson | A61B 17/7037 606/267 |
| 9,788,865 B2 * | 10/2017 | Matthis | A61B 17/7037 |
| 2006/0241600 A1 * | 10/2006 | Ensign | A61B 17/7005 81/52 |
| 2007/0135817 A1 * | 6/2007 | Ensign | A61B 17/7007 606/96 |

(Continued)

*Primary Examiner* — Lynnsy M Summitt
(74) *Attorney, Agent, or Firm* — Sorell, Lenna & Schmidt, LLP (57) ABSTRACT

A spinal construct comprises a fastener including a head. A member includes an inner surface defining a cavity configured for disposal of the head and a groove configured for disposal of a band that is engageable with the head to connect the fastener and the member. The member includes a transverse rod. A coupling member is engageable with the inner surface. Implants, systems, instruments and methods are disclosed.

20 Claims, 7 Drawing Sheets

(56) References Cited

U.S. PATENT DOCUMENTS

| | | | |
|---|---|---|---|
| 2007/0270839 A1 | 11/2007 | Jeon et al. | |
| 2007/0288004 A1* | 12/2007 | Alvarez | A61B 17/7032 606/86 A |
| 2011/0040338 A1* | 2/2011 | Jackson | A61B 17/7032 606/305 |
| 2011/0093021 A1 | 4/2011 | Fanger et al. | |
| 2011/0098755 A1* | 4/2011 | Jackson | A61B 17/7008 606/305 |
| 2011/0270325 A1* | 11/2011 | Keyer | A61B 17/7007 606/305 |
| 2012/0101533 A1* | 4/2012 | Purcell | A61B 17/7037 606/305 |
| 2012/0109218 A1* | 5/2012 | Farris | A61B 17/8685 606/305 |
| 2016/0015429 A1* | 1/2016 | Butler | A61B 17/7035 606/278 |
| 2016/0206357 A1* | 7/2016 | Whipple | A61B 17/7037 |
| 2016/0262798 A1* | 9/2016 | Rezach | A61B 17/7007 |
| 2016/0367292 A1* | 12/2016 | Nichols | A61B 17/7041 |
| 2017/0245898 A1* | 8/2017 | May | A61B 17/7037 |
| 2017/0281241 A1* | 10/2017 | Jackson | A61B 17/7037 |

* cited by examiner

SPINAL CONSTRUCT

TECHNICAL FIELD

The present disclosure generally relates to medical devices for the treatment of spinal disorders, and more particularly to a surgical implant system including a bone fastener and a related method.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, microdiscectomy, corpectomy, decompression, laminectomy, laminotomy, foraminotomy, facetectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a spinal construct is provided. The spinal construct comprises a fastener including a head. A member includes an inner surface defining a cavity configured for disposal of the head and a groove configured for disposal of a band that is engageable with the head to connect the fastener and the member. The member further includes a transverse rod. A coupling member is engageable with the inner surface. In some embodiments, implants, systems, instruments and methods are disclosed.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system and related methods of use disclosed are discussed in terms of medical devices for the treatment of musculoskeletal disorders and more particularly, in terms of a surgical system including a bone fastener. In one embodiment, a spinal implant system includes a spinal construct having a spinal rod and a screw receiver. In some embodiments, the spinal construct includes a reduced dorsal profile with vertebrae.

In some embodiments, the spinal implant system comprises a longitudinal element, such as, for example, a rod including a screw receiver member. In some embodiments, the screw receiver member is configured to facilitate engagement with a head of a bone screw. In some embodiments, the spinal implant system comprises a screw receiver including a retaining member, a compression member and/or a housing. In some embodiments, the housing may be monolithically formed with the rod. In some embodiments, the housing is welded and/or connected by fastening elements with the rod. In some embodiments, the housing is configured to facilitate connection with the bone screw head. In some embodiments, the rod is connected with the screw by various screw connection mechanisms, such as, for example, a collet and/or taper lock. In some embodiments, the rod includes one or a plurality of screw receivers.

In some embodiments, the spinal implant system includes a rod configured for attachment to a spherical head of a bone screw and connectable with one or a plurality of tulip head bone screws and/or pedicle screws. In some embodiments, the spinal implant system includes a screw receiver attached with a single bone screw without a tulip head and including a rod connected with one or a plurality of tulip head bone screws and/or pedicle screws. In some embodiments, the spinal implant system includes a screw receiver attached with one or a plurality of bone screws without a tulip head. In some embodiments, the spinal implant system includes a screw receiver including a rod connected with a first bone screw without a tulip head at a first end and a second bone screw without a tulip head at a second end such that the rod attaches the bone screws. In some embodiments, the spinal implant system provides a low profile spinal construct that connects one or more bone screws without a tulip head with one or a plurality of separate tulip head bone screws and/or pedicle screws.

In some embodiments, the spinal implant system is employed with a method such that the spinal construct includes one or a plurality of tulip head bone screws and/or pedicle screws fastened along one or more vertebral levels and a screw receiver connected with a bone screw without a tulip head fastened to a single vertebral level. In some embodiments, the spinal construct includes a rod having one or a plurality screw receivers configured for connection with one or a plurality of bone screws. In some embodiments, the spinal construct can be utilized as a superior connection to reduce a profile adjacent to a non-fused facet joint.

In some embodiments, the spinal construct includes a locking member. In some embodiments, the spinal construct includes a compression member. In some embodiments, the spinal construct includes a retaining member expansion chamber. In some embodiments, the spinal construct includes a retaining member. In some embodiments, the spinal construct includes a bone screw. In some embodiments, the spinal construct includes a screw receiver.

In some embodiments, the spinal implant system is employed with a method of assembly such that the locking member is preassembled with the rod, a retaining member and a compression member. In some embodiments, the locking member is connected with the compression member such that the members translate along an axis of the locking member as the locking member is actuated and/or rotated. In some embodiments, the rod is monolithically formed with the screw receiver. In some embodiments, the rod is welded and/or integrally assembled with the screw receiver.

In some embodiments, the spinal construct includes a screw receiver having a rod extending therefrom such that the rod is extends in an offset orientation to accommodate anatomy and/or implants disposed at other spine levels. In some embodiments, the rod extends in an offset dorsal orientation and/or an offset coronal orientation.

In some embodiments, the spinal implant system comprises a modular screw system. In some embodiments, the spinal implant system comprises base component that is pre-assembled with a bone screw. In some embodiments, the spinal implant system comprises screw assemblies and screw receiver assemblies that may be joined together during manufacturing or intra-operatively, such as, for example, during a surgical procedure in an operating room.

In some embodiments, a bone screw assembly includes a head having a base and a screw shaft. In some embodiments, a screw receiver includes a crown, a body and a snap ring. In some embodiments, a snap ring is engaged in a retaining groove in the body and provisionally engaged to the crown. In some embodiments, a snap ring is engaged to a part, such as, for example, a sleeve that maintains the snap ring centered. In some embodiments, the present system is employed with a method of assembly such that during assembly the base drives and/or translates the crown or sleeve upwards to force the snap ring to expand and disengage the crown. In some embodiments, the method includes the step of engaging the head with the screw receiver such that the snap ring engages a retaining groove in the screw receiver and creates a permanent assembly of a bone fastener.

In some embodiments, the present system is employed with a method of assembly including the step of initially engaging a screw receiver with a head of a bone screw. In some embodiments, the method includes the step of expanding a snap ring such that the snap ring is expanded by the head forcing a crown upwards in the screw receiver. In some embodiments, this configuration allows the crown to disengage from the snap ring. In some embodiments, the method includes the step of collapsing the snap ring such that as the head travels into the screw receiver, the snap ring collapses in a retaining groove and the bone fastener is permanently assembled.

In some embodiments, the spinal implant system comprises a spinal construct that can be assembled on a surgical table or in-situ. In some embodiments, the spinal construct is assembled with a force of less than 50 Newtons (N). In some embodiments, the spinal construct is selectively coupled with a non-instrumented assembly. In some embodiments, the non-instrumented assembly comprises manually engaging a head of a bone screw with a screw receiver. In some embodiments, the non-instrumented assembly comprises manually engaging the head in a pop-on engagement with the screw receiver. In some embodiments, a force required to manually engage the head with the screw receiver in a non-instrumented assembly is in a range of 2 to 50 N. In some embodiments, a force required to manually engage the head with the screw receiver in a non-instrumented assembly is in a range of 5 to 10 N. In some embodiments, a head of a bone screw is manually engaged with a screw receiver in a non-instrumented assembly, as described herein, such that removal of the screw receiver from the head requires a force and/or a pull-out strength of at least 5000 N. In some embodiments, this configuration provides manually engageable components of a bone fastener that are assembled without instrumentation, and subsequent to assembly, the assembled components have a selected pull-out strength and/or can be pulled apart, removed and/or separated with a minimum required force.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 1:
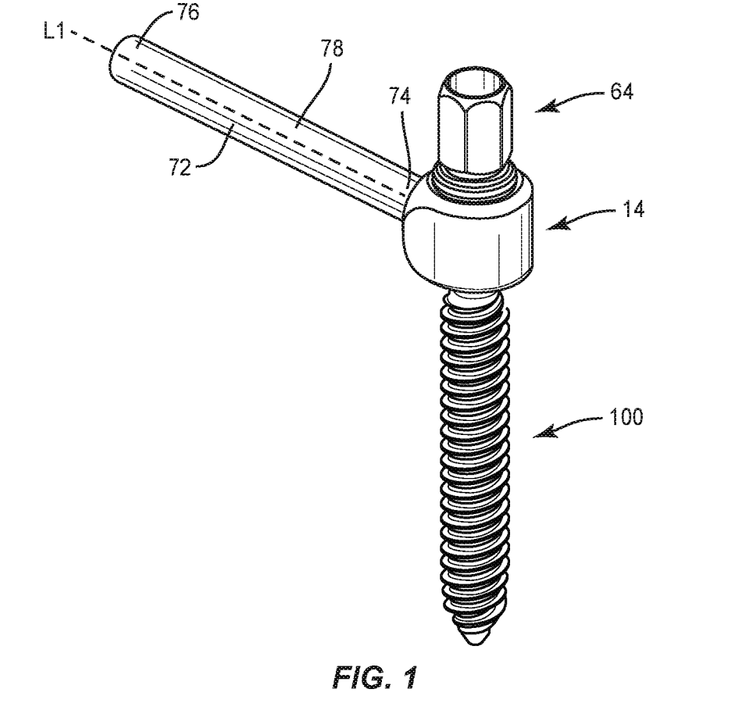
FIG. 1 is a perspective view of components of one embodiment of a surgical system in accordance with the principles of the present disclosure.
Figure 2:
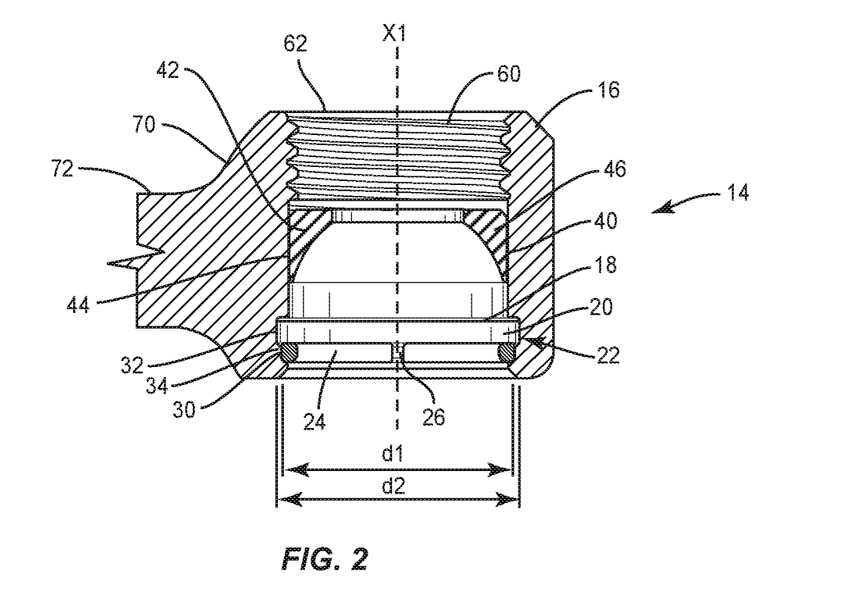
FIG. 2 is a cross section view of components of the system shown in FIG. 1.
Figure 3:
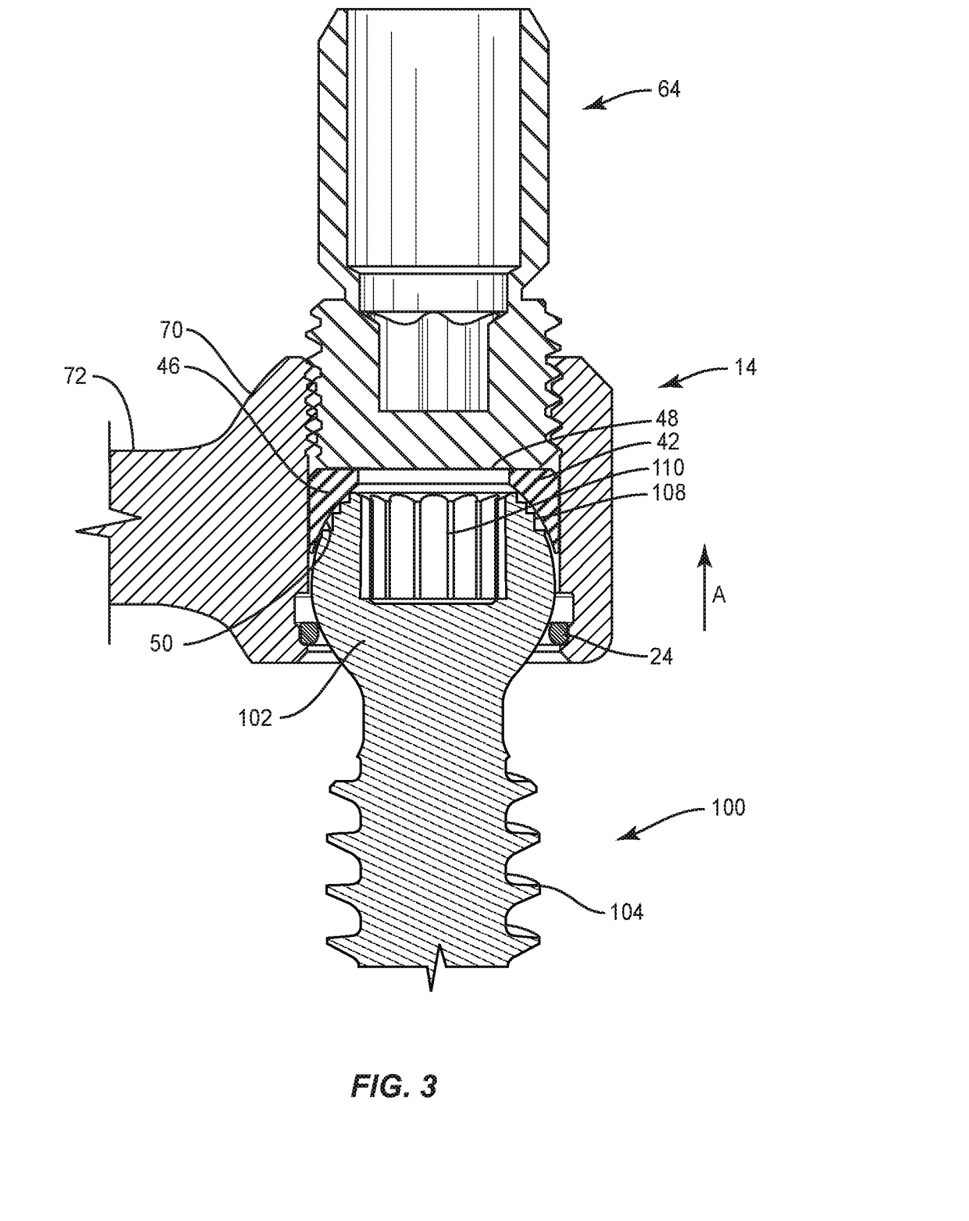
FIG. 3 is a cross section view of the components shown in FIG. 1.

The following discussion includes a description of a surgical system including a spinal construct, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-3, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal construct 12. Spinal implant system 10 is employed, for example, with an open or mini-open, minimal access and/or minimally invasive including percutaneous surgical technique and includes one or more spinal constructs 12 for treatment at a surgical site within a body of a patient, for example, a section of a spine to treat various spine pathologies, such as those described herein. In some embodiments, the components of spinal implant system 10 are configured to deliver and introduce components of a spinal construct 12 that includes implants, such as, for example, one or more receivers, spinal rods, bodies, sleeves, connectors, plates and/or fasteners. Spinal construct 12 forms one or more components of a surgical treatment implanted with tissue for positioning and alignment to stabilize a treated section of vertebrae. Spinal construct 12 provides a low or reduced profile construct disposed along vertebrae, for example, adjacent a non-fused facet joint, as described.

Spinal construct 12 includes a fastener, such as, for example, a bone screw 100 connectable with a member, such as, for example, a receiver 14. Screw receiver 14 includes a wall 16. Wall 16 includes an inner surface 18 that defines a cavity 20. Cavity 20 is configured for disposal of a head 102 of bone screw 100, as described herein. Wall 16 extends along an axis X1, as shown in FIG. 2. In some embodiments, wall 16 may extend in alternate configurations relative to axis X1, such as, for example, arcuate, offset, staggered and/or angled portions. Cavity 20 is substantially circular. In some embodiments, all or only a portion of cavity 20 may have alternate cross section configurations, such as, for example, closed, V-shaped, W-shaped, oval, U-shaped, oblong, polygonal, irregular, uniform, non-uniform, offset, staggered, and/or tapered. In some embodiments, spinal construct 12 may include one or a plurality of receivers 14.

Surface 18 defines a groove 22 configured for disposal of a band, such as, for example, a circumferential ring 24. Ring 24 includes a circumference that extends between ends defining an opening, such as, for example, a gap 26, which facilitates expansion and contraction. Groove 22 includes a portion, such as for, example, a circumferential channel 30 having a diameter d1 and a portion, such as for, example, a circumferential channel 32 having a diameter d2, as shown in FIG. 2. In some embodiments, diameter d2 is greater than diameter d1.

Channel 32 is disposed adjacent and proximal to channel 30. Channel 32 is separate from channel 30 by a protrusion, such as, for example, a lip 34. In some embodiments, bone screw 100 is manually engageable with receiver 14 and/or bone screw 100 is coupled with receiver 14 in a non-instrumented assembly such that ring 24 translates from and into channels 30, 32, and over lip 34, as described herein. Ring 24 is expandable and resilient between a contracted and/or capture orientation and an expanded orientation, as described herein. In some embodiments, ring 24 facilitates manual engagement of receiver 14 and bone screw 100 such that receiver 14 is attached with bone screw 100 in a non-instrumented assembly, as described herein.

In some embodiments, wall 16 defines a slot 40 configured for disposal of a part, such as, for example, a crown 42, as described herein. Slot 40 is defined by a surface 44 of wall 16. In some embodiments, all or only a portion of surface 44 may have alternate surface configurations to enhance engagement with crown 42, such as, for example, rough, arcuate, undulating, mesh, porous, semi-porous, dimpled and/or textured.

Crown 42 includes a wall 46 having an end surface 48 and an end surface 50, as shown in FIG. 3. Surface 48 is configured for engagement with a coupling member, as described herein. Surface 50 defines a curved portion of crown 42 engageable with bone screw 100, as described herein. In some embodiments, all or only a portion of surface 50 may have alternate cross section configurations, such as, for example, oval, oblong, polygonal, irregular, uniform, non-uniform, offset, staggered, and/or tapered.

Receiver 14 includes an inner surface 60. A portion of surface 60 includes a thread form 62. Thread form 62 is configured for engagement with a coupling member, such as, for example, a setscrew 64 to fix position and/or orientation of bone screw 100 within cavity 20 relative to one or more components of spinal construct 12 and/or tissue. In some embodiments, surface 60 may be disposed with the coupling member in alternate fixation configurations, such as, for example, friction fit, pressure fit, locking protrusion/recess, locking keyway and/or adhesive. In some embodiments, all or only a portion of surface 60 may have alternate surface configurations to enhance engagement with setscrew 64 such as, for example, rough, arcuate, undulating, mesh, porous, semi-porous, dimpled and/or textured.

Setscrew 64 is actuated for translation along axis X1 to fix or release bone screw 100 and receiver 14. Setscrew 64 is configured for engagement with crown 42 and/or head 102 to facilitate fixation of bone screw 100 with receiver 14. Setscrew 64 is disposable between a non-locking orientation such that bone screw 100 is moveable relative to receiver 14 and a locked orientation such that setscrew 64 fixes bone screw 100 with receiver 14 relative to one or more components of spinal construct 12 and/or tissue.

In some embodiments, setscrew 64 is pre-assembled with receiver 14, for example, setscrew 64 can be connected with receiver in-situ or on a back table of an operating room during a surgical procedure, or at a manufacturing facility. In some embodiments, setscrew 64 is integrally connected with receiver 14. In some embodiments, setscrew 64 is connected with crown 42 such that actuation of setscrew 64 simultaneously axially translates setscrew 64 and crown 42 relative to receiver 14 to fix position and/or orientation of bone screw 100 within cavity 20 relative to one or more components of spinal construct 12 and/or tissue.

Receiver 14 includes an outer surface 70. A spinal rod 72 extends from surface 70 along an axis L1. Rod 72 extends transverse to axis X1. In some embodiments, rod 72 may extend in alternate orientations relative to axis X1, such as, for example, arcuate, tapered, perpendicular, parallel and/or other angular orientations such as acute or obtuse, co-axial and/or may be offset or staggered. Rod 72 extends between an end 74 and an end 76. In some embodiments, rod 72 may have various cross section configurations, such as, for example, circular, oval, oblong, polygonal, irregular, uniform, non-uniform, variable, offset and/or tapered. Rod 72 includes a surface 78 configured for connection with a receiver of one or a plurality of bone fasteners, as described herein.

Figure 4:
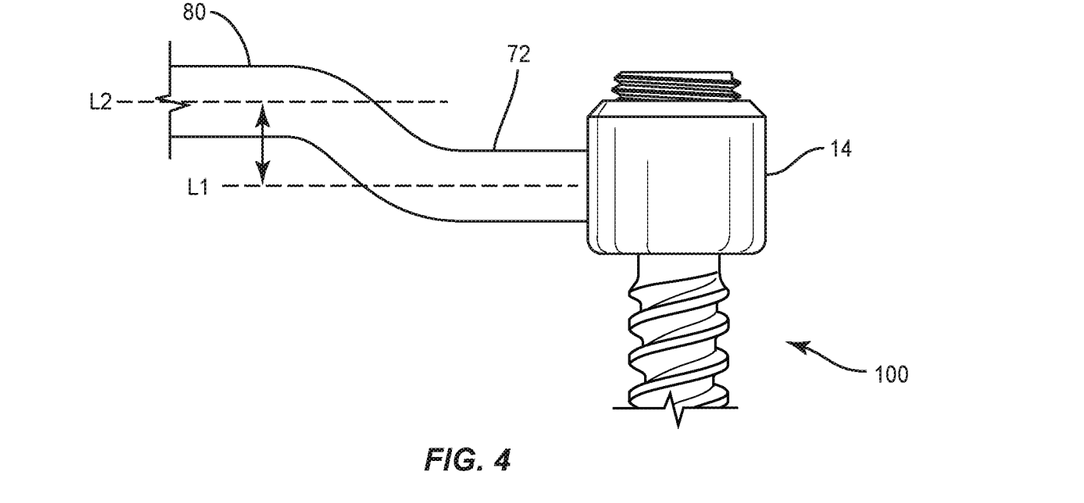
FIG. 4 is a side view of components of one embodiment of a surgical system in accordance with the principles of the present disclosure.
Figure 5:
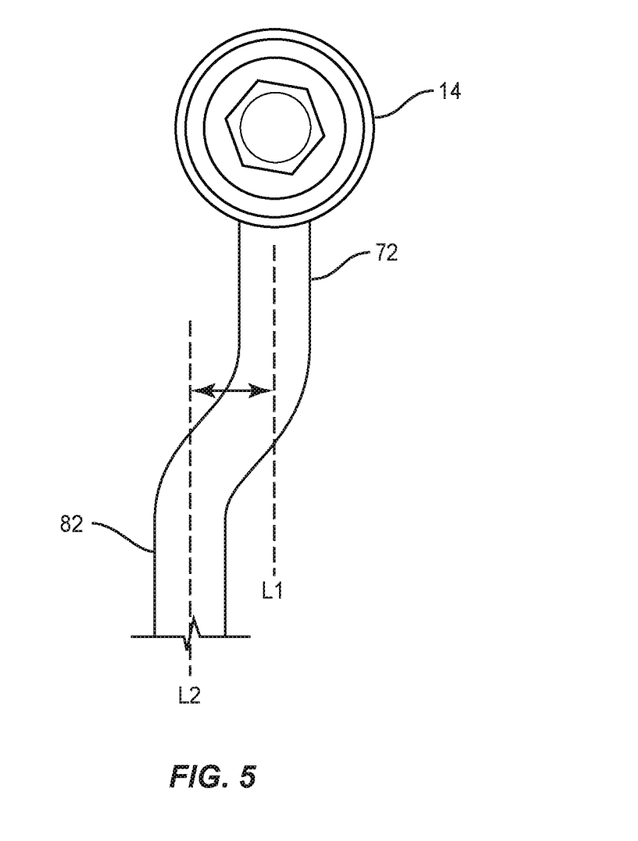
FIG. 5 is a side view of components of one embodiment of a surgical system in accordance with the principles of the present disclosure.

In some embodiments, rod 72 is monolithically formed with receiver 14. In some embodiments, rod 72 is integrally connected with receiver 14 by welding. In some embodiments, rod 72 is integrally connected with receiver 14 by fastening elements and/or instruments to facilitate connection. In one embodiment, as shown in FIG. 4, rod 72 extends along axis L1 and includes an extension 80 that extends along an axis L2. Extension 80 is dorsally offset such that axis 12 is offset relative to axis L1. Extension 80 is connected to rod 72 via an angled transition to orient rod 72 dorsally and provide clearance for an existing spinal implant and/or anatomy. In one embodiment, as shown in FIG. 5, rod 72 extends along axis L1 and includes an extension 82 that extends along an axis L2. Extension 82 is coronally offset such that axis L2 is offset relative to axis L1. Extension 82 is connected to rod 72 via an angled transition to orient rod 72 coronally and provide clearance for an existing spinal implant and/or anatomy. In some embodiments, rod 72 can be offset in various axial, planar and/or other orientations, such as, for example, a transverse plane, a coronal plane, a sagittal plane, perpendicular and parallel.

Bone screw 100 includes head 102 and a shaft 104. Head 102 includes a spherical configuration. In some embodiments, head 102 includes a surface 106 that defines a plurality of ridges 108 to improve purchase of head 108 with crown 42. Head 102 includes a tool engaging portion 110 configured to engage a surgical tool or instrument, as described herein. In some embodiments, portion 110 includes a hexagonal cross-section to facilitate engagement with a surgical tool or instrument, as described herein. In some embodiments, portion 110 may have alternative cross-sections, such as, for example, rectangular, polygonal, hexalobe, oval, or irregular.

Shaft 104 is configured to penetrate tissue, such as, for example, bone. In some embodiments, shaft 104 includes an outer surface having an external thread form. In some embodiments, the external thread form may include a single thread turn or a plurality of discrete threads.

In some embodiments, receiver 14 is manually engageable with head 102 in a non-instrumented assembly such that ring 24 translates from disposal with channel 30 and into channel 32, as described herein. In some embodiments, manual engagement and/or non-instrumented assembly of receiver 14 and head 102 includes coupling without use of separate and/or independent instrumentation engaged with the components to effect assembly. In some embodiments, manual engagement and/or non-instrumented assembly includes a practitioner, surgeon and/or medical staff grasping receiver 14 and bone screw 100 and forcibly assembling the components. In some embodiments, manual engagement and/or non-instrumented assembly includes a practitioner, surgeon and/or medical staff grasping receiver 14 and bone screw 100 and forcibly snap fitting the components together, as described herein. In some embodiments, manual engagement and/or non-instrumented assembly includes a practitioner, surgeon and/or medical staff grasping receiver 14 and bone screw 100 and forcibly pop fitting the components together and/or pop fitting receiver 14 onto bone screw 100, as described herein. In some embodiments, a force in a range of 2-50 N is required to manually engage receiver 14 and bone screw 100 and forcibly assemble the components. For example, a force in a range of 2-50 N is required to snap fit and/or pop fit assemble receiver 14 and bone screw 100. In some embodiments, a force in a range of 5-10 N is required to manually engage receiver 14 and bone screw 100 and forcibly assemble the components. For example, a force in a range of 5-10 N is required to snap fit and/or pop fit assemble receiver 14 and bone screw 100.

In some embodiments, spinal construct 12 includes one or a plurality of bone fasteners 150. Bone fastener 150 comprises a head 152 and an elongated shaft 154 configured for penetrating tissue. Head 152 includes a receiving portion configured for disposal of rod 72. In some embodiments, head 152 includes tulip heads and/or bone fastener 150 comprises a pedicle screw. In some embodiments, head 152 is manually engageable with shaft 154 in a non-instrumented assembly, as described herein.

In some embodiments, one or more of bone fasteners 150 and/or bone screws 100 may be engaged with tissue in various orientations, such as, for example, series, parallel, offset, staggered and/or alternate vertebral levels. In some embodiments, one or more fasteners 150 and/or bone screws 100 may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

Figure 6:
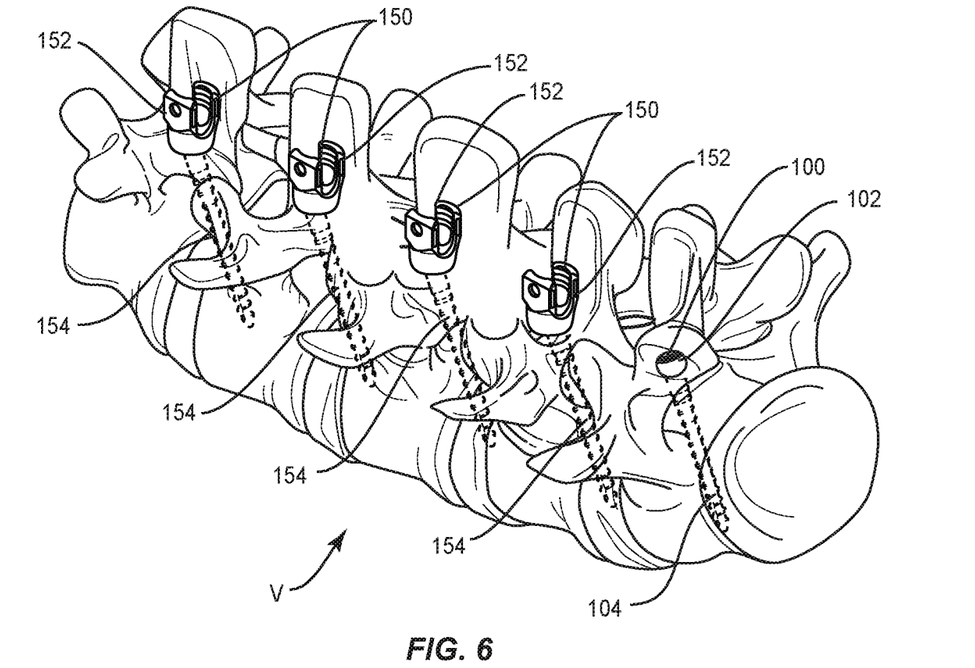
FIG. 6 is a perspective view of components of one embodiment of a surgical system in accordance with the principles of the present disclosure disposed with vertebrae.
Figure 7:
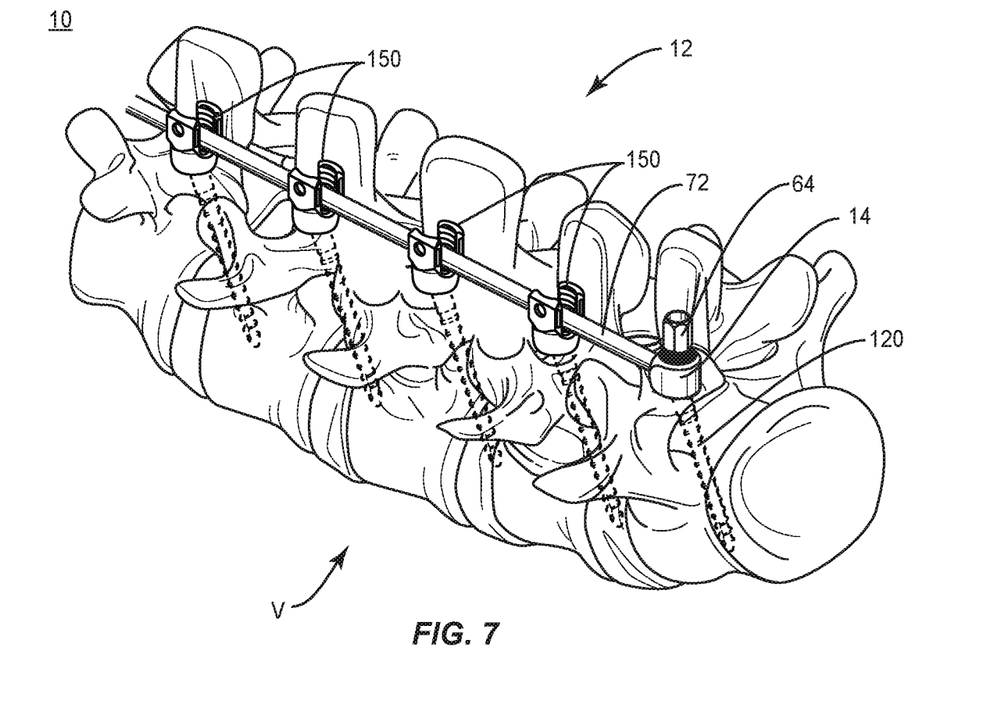
FIG. 7 is a perspective view of components of one embodiment of a surgical system in accordance with the principles of the present disclosure disposed with vertebrae.
Figure 8:
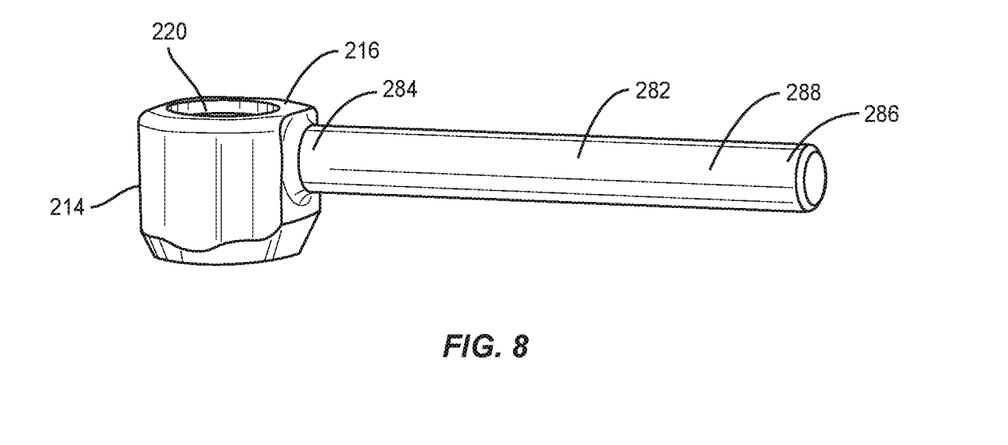
FIG. 8 is a perspective view of components of one embodiment of a surgical system in accordance with the principles of the present disclosure.

In assembly, operation and use, as shown in FIGS. 6 and 7, spinal implant system 10, similar to the systems and methods described herein, includes spinal construct 12 and is employed with a surgical procedure for treating disorders of the spine, such as those described herein. In some embodiments, one or all of the components of spinal implant system 10 can be delivered as a pre-assembled device or can be assembled in situ.

The surgical treatment including spinal construct 12 can be used for correction and alignment in stabilization of a treated section of vertebrae V. In an exemplary use, a medical practitioner obtains access to a surgical site including vertebrae V via a posterior surgical approach. In some embodiments, the surgical site may be accessed in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area.

Spinal construct 12 is disposed with vertebrae V in connection with the surgical procedure. In some embodiments, one or more spinal constructs 12 are disposed in a linear orientation along vertebrae V. In some embodiments, one or more spinal constructs 12 are disposed with vertebrae V in alternate orientations relative to each other, such as, for example, parallel, perpendicular, adjacent, co-axial, arcuate, offset, staggered, transverse, angular and/or relative posterior/anterior orientations and/or at alternate vertebral levels.

Pilot holes are made in vertebrae V in a selected orientation. Bone fasteners 150 and bone screw 100, as described herein, are aligned with the pilot holes and fastened with the tissue of vertebrae V. In some embodiments, bone fasteners 150 are disposed in a selected orientation, as described herein, with one or more vertebral levels of vertebrae V. In some embodiments, bone screw 100 is disposed in a selected orientation with a single vertebral level of vertebrae V.

The components of spinal construct 12 are assembled, which includes disposing crown 42 with slot 40, ring 24 with channel 30 and aligning head 102 with receiver 14, as descried herein. Bone screw 100 is connected with receiver 14, as shown in FIG. 7, and rod 72 extends from receiver 14 in a selected orientation, as described herein, relative to bone fasteners 150 and/or vertebrae V.

Head 102 translates through and relative to ring 24, over lip 34 into channel 32, into an expanded orientation, as described herein. Head 102 engages crown 42 and ring 24 is resiliently biased to the capture orientation such that receiver 14 is attached with bone screw 100, as described herein. Disengagement of bone screw 100 from receiver 14 is resisted and/or prevented.

Rod 72 is oriented and/or manipulated such that surface 78 is disposed with heads 152 of bone fasteners 150 along one or more vertebral levels of vertebrae V. Setscrew 64 is disposed in a non-locking orientation and actuated for translation along axis X1. Setscrew 64 engages crown 42/head 102, and is disposed in a locked orientation to fix the selected position and orientation of bone screw 100 and receiver 14 with vertebrae V. In some embodiments, setscrews (not shown) are fastened with heads 152 and surface 78 to fix the selected position and orientation of rod 72 with bone fasteners 150.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

Figure 9:
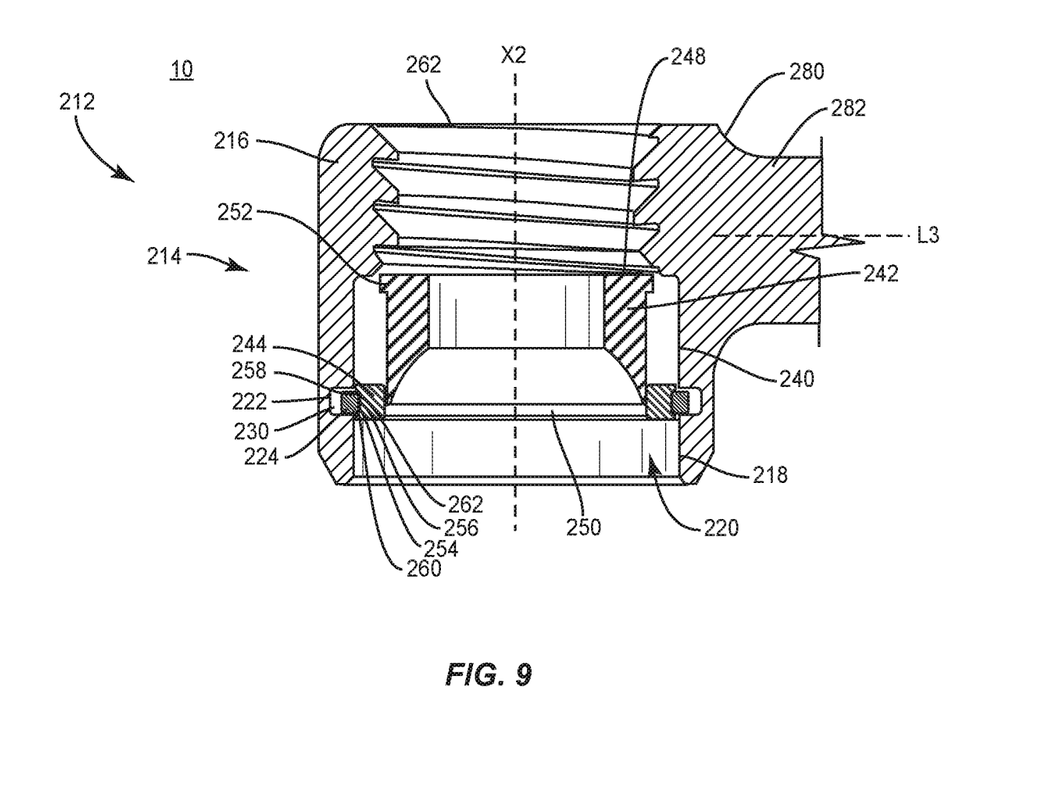
FIG. 9 is a cross section view of the components shown in FIG. 8.
Figure 10:
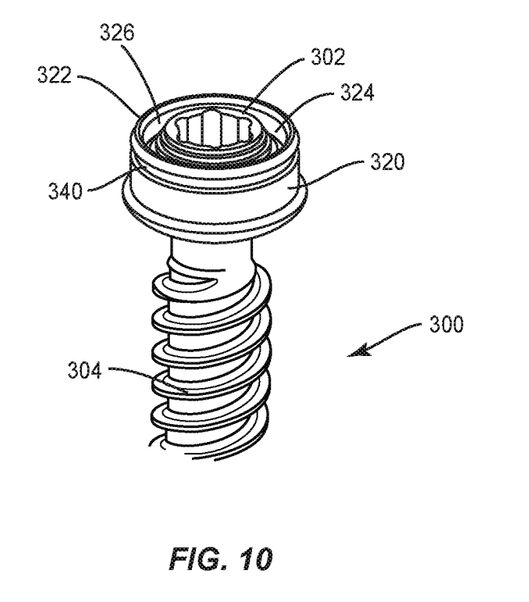
FIG. 10 is a perspective view of components of one embodiment of a surgical system in accordance with the principles of the present disclosure.

In one embodiment, as shown in FIGS. 8-13, spinal implant system 10, similar to the systems and methods described herein, includes a spinal construct 212, similar to spinal construct 12 described herein. Spinal construct 212 includes a receiver 214, similar to receiver 14 described herein. Receiver 214 includes a wall 216 having a surface 218 that defines a cavity 220. Wall 216 extends along an axis X2, as shown in FIG. 9. Cavity 220 is configured for disposal of a head 302 of a bone screw 300, as described herein.

Surface 218 defines a groove 222 configured for disposal of a circumferential ring 224, similar to ring 24 described herein. Ring 224 includes a circumference that extends between ends defining a gap, which facilitates expansion and contraction thereof. Groove 222 includes a circumferential channel 230 that accommodates expansion of ring 224. In some embodiments, upon disposal of ring 224 with groove 222, the surface of groove 222 resists and/or prevents axial translation of ring 224 relative to axis X2.

Ring 224 is expandable and resilient between a contracted and/or capture orientation, and an expanded orientation, similar to that described herein. Ring 224 facilitates manual engagement of receiver 214 and bone screw 300 such that a receiver 214 is attached with bone screw 300 in a non-instrumented assembly, as described herein. In some embodiments, ring 224 is expandable and resilient between a contracted and/or capture orientation and an expanded orientation for assembly of receiver 214 with bone screw 300, as shown and described for example with regard to FIGS. 11-13.

Surface 218 defines a slot 240 configured for disposal of a part, such as, for example, a crown 242 and a sleeve 244. Crown 242 is configured for disposal within cavity 220. Crown 242 includes a wall 246 having an end surface 248 and an end surface 250. Surface 248 is configured for engagement with a setscrew (not shown), similar to setscrew 64 described herein. Surface 250 defines a curved portion of crown 242 configured for engagement with head 302 of bone screw 300, as described herein.

Surface 248 defines a flange 252 configured for mating engagement with a portion of surface 218. In some embodiments, flange 252 engages a portion of surface 218 in a keyed connection. In some embodiments, engagement of flange 252 and surface 218 prevents rotation and/or axial translation of crown 242 relative to surface 218 of receiver 214.

Sleeve 244 includes a surface 254 that defines a cavity, such as, for example, a groove 256. In some embodiments, groove 256 extends about all or a portion of surface 254. Groove 256 includes a surface 258 and a surface 260. Surface 258 is disposed at an angle relative to axis X2 to define a ramp. Surface 260 is disposed at an angle relative to axis X2 to define a ramp. The ramps of surfaces 258, 260 are oriented in spaced apart relation. An intermediate surface 262 is disposed between the ramps. Surface 262 is substantially even and circumferentially disposed about sleeve 244. In some embodiments, the ramps of surfaces 258, 260 are selectively inclined to resist and/or prevent displacement of ring 224 from channel 230 to provisionally fix sleeve 244 with receiver 214. In some embodiments, the inclination of the ramps of surfaces 258, 260 facilitate disengagement of ring 224 from groove 256 upon axial translation of sleeve 244, as described herein. In some embodiments, surfaces 258, 260 are oriented substantially perpendicular to axis X2. In some embodiments, groove 256 does not include inclined surfaces, as described above, and alternatively includes a protrusion or a lip configured to engage ring 224.

Figure 11:
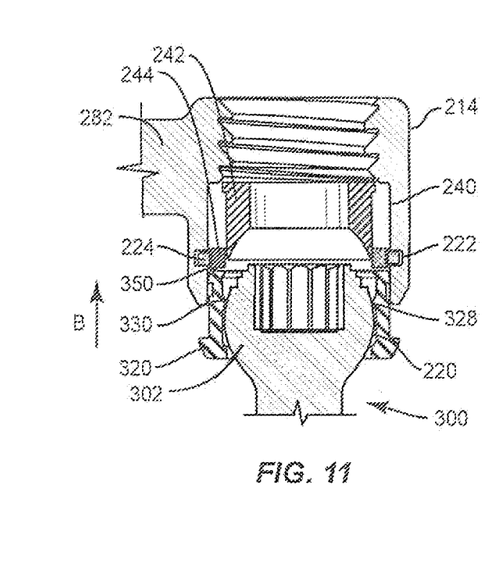
FIGS. 11, 12, 13 are cross section views of components of one embodiment of a surgical system illustrating assembly.
Figure 13:
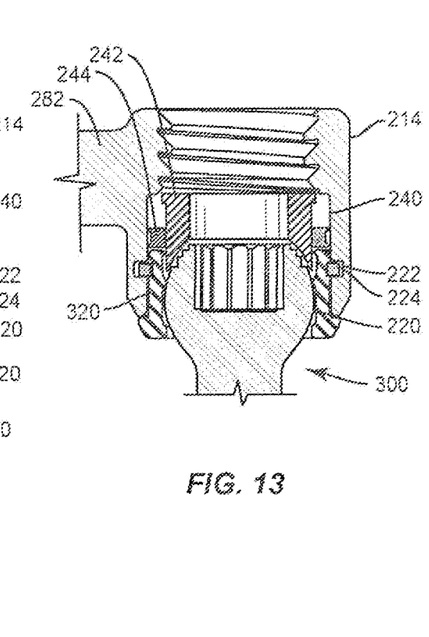

Sleeve 244 is configured for translation within slot 240 along surface 218. Sleeve 244 translates relative to crown 242 and receiver 214 within slot 240. Translation of sleeve 244 within slot 240 moves sleeve 244 between a configuration, as shown in FIG. 11, such that ring 224 is disposed within channel 230 and groove 256 to provisionally fix sleeve 244 relative to receiver 214 and a configuration, as shown in FIG. 13, such that ring 224 remains disposed within channel 230 and a base 320, attached with bone screw 300, to fix bone screw 300 with receiver 214, as described herein.

Bone screw 300 includes a head 302 and a shaft 304. Head 302 includes a spherical configuration. In some embodiments, head 302 includes a surface 306 that defines a plurality of ridges 308 to improve purchase of head 308 with crown 242. Head 302 includes a tool engaging portion 310 configured to engage a surgical tool or instrument, as described herein. In some embodiments, portion 310 includes a hexagonal cross-section to facilitate engagement with a surgical tool or instrument, as described herein. In some embodiments, portion 310 may have alternative cross-sections, such as, for example, rectangular, polygonal, hex-alobe, oval, or irregular.

Shaft 304 is configured to penetrate tissue, such as, for example, bone. In some embodiments, shaft 304 includes an outer surface having an external thread form. In some embodiments, the external thread form may include a single thread turn or a plurality of discrete threads.

Bone screw 300 includes base 320, which has a wall 322. Wall 322 includes a surface 324. Surface 324 defines a cavity 326 configured for disposal of head 302. Surface 324 facilitates engagement of head 302 with base 320 via a pressure and/or force fit connection.

In some embodiments, surface 324 includes mating elements, such as, for example, index elements 328. In some embodiments, index elements 328 include a protrusion 330 configured to limit rotation about a single axis disposed in a plane relative to receiver 214. In some embodiments, rotation of shaft 304 in a second plane is resisted and/or prevented due to the interface of head 302 and index elements 328. In some embodiments, receiver 214 is connected to a selected crown 242 to comprise a multi-axial receiver. In some embodiments, receiver 214 is connected to a selected crown 242 to comprise a uni-axial receiver. In some embodiments, receiver 214 is connected to a selected crown 242 to comprise a fixed axis receiver to resist and/or prevent movement of shaft 304 relative to receiver 214. In some embodiments, receiver 214 comprises one or more fixed axis receivers, multi-axial receivers and uni-axial receivers. In some embodiments, spinal implant system 10 comprises a spinal implant kit, which includes alternate crowns, such as those described herein. In some embodiments, spinal implant system 10 comprises a spinal implant kit, which includes alternate receivers, screws and crowns.

In some embodiments, base 320 may be disposed with head 302 in alternate fixation configurations, such as, for example, friction fit, pressure fit, locking protrusion/recess, locking keyway and/or adhesive. Base 320 is configured for rotation relative to head 302. In some embodiments, base 320 is configured for rotation in range of 360 degrees relative to head 302 to facilitate positioning of shaft 304 with tissue. In some embodiments, base 320 is configured for selective rotation in range of 360 degrees relative to and about head 302 such that shaft 304 is selectively aligned for rotation in a plane relative to receiver 214, and rotation in a second plane is resisted and/or prevented.

Wall 322 includes a surface 340. Surface 340 defines a groove 342. Groove 342 includes a surface 344 and a surface 346. Surfaces 344, 346 are oriented substantially perpendicular to axis X2. In some embodiments, surfaces 344, 346 may be disposed in various orientations and/or inclinations, such as, for example, transverse and/or at angular orientations, such as acute or obtuse relative to axis X2. Surface 344 is oriented in spaced apart relation relative to surface 346. An intermediate surface 348 is disposed between surfaces 344, 346. Surface 348 is substantially even and circumferentially disposed about groove 342. In some embodiments, surfaces 344, 346, 348 may be disposed about all or only a portion of groove 342. Groove 342 is configured for disposal of ring 224 to prevent displacement of ring 224 from channel 230 and to permanently fix receiver 214 with bone screw 300, as shown in FIG. 13. Base 320 is configured for axial translation relative to head 302 within slot 240, as described herein.

Figure 12:
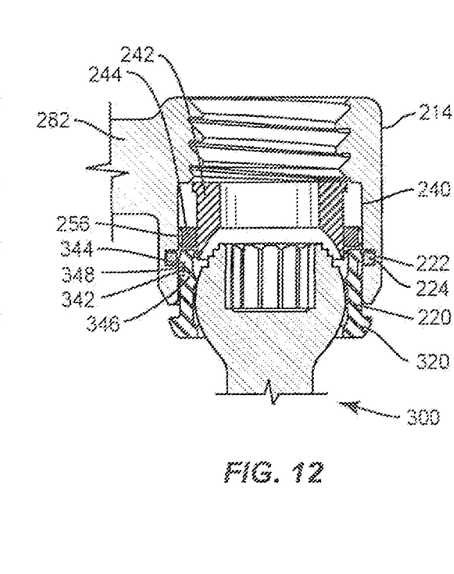

For example, base 320 is assembled with head 302 and a surface 350 engages sleeve 244 to release sleeve 244 from ring 224, as shown in FIG. 11. As base 320 engages sleeve 244 and translates, in a direction shown by arrow B in FIG. 11, the ramp of surface 260 engages ring 224 and surface 260 slides over ring 224 to release sleeve 244 from ring 224. Ring 224 expands into channel 230, as shown in FIG. 12. With ring 224 expanded into channel 230, base 320 and head 302 axially translate relative to receiver 214 within slot 240 to align groove 342 with channel 230. Expansion of ring 224 via engagement with surface 260 facilitates axial translation of bone screw 300 into slot 240. Alignment of groove 342 with channel 230 allows ring 224 to resiliently contract to the capture orientation, as shown in FIG. 13, for disposal of ring 224 within groove 342 and channel 230. Ring 224 is fixed within channel 230 and groove 342. Surfaces 344, 346 resist and/or prevent disengagement of ring 224 from channel 230 and groove 342 to permanently assemble bone screw 300 with receiver 214.

Receiver 214 includes an inner surface 270. A portion of surface 270 includes a thread form 272. Thread form 272 is configured for engagement with the setscrew, described herein. The setscrew is actuated for translation along axis X2 to fix or release bone screw 300 and receiver 214, similar to that described herein. The setscrew is configured for engagement with crown 242 and/or head 302 to facilitate fixation of bone screw 300 with receiver 214. The setscrew is disposable between a non-locking orientation such that bone screw 300 is moveable relative to receiver 214 and a locked orientation such that the setscrew fixes bone screw 300 with receiver 214 relative to one or more components of spinal construct 212 and/or tissue, similar to that described herein.

Receiver 214 includes an outer surface 280. A rod 282, similar to rod 72 described herein, extends from surface 280 along an axis L3. In some embodiments, rod 282 extends transverse to axis X2. In some embodiments, rod 282 is connectable with one or a plurality of fasteners, similar to rod 72 described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
    a fastener comprising a head and a shaft connected to the head, the fastener including a monolithic base, the head being disposed in the base such that the base extends 360 degrees about the head, the base including a groove;
    a member including a body having opposite top and bottom walls and a side wall extending from the top wall to the bottom wall, the member defining a circular bore extending through the top wall, an opening extending through the bottom wall, a cavity configured for disposal of the head, and a groove configured for disposal of a band, the member further including a transverse rod extending outwardly from the side wall;
    a crown disposed in the cavity; and
    a part disposable with the cavity and comprising a groove, wherein the base is configured to move relative to the member to move the spinal construct from a first orientation in which the band is disposed in the groove of the part and the groove of the member to a second orientation in which the band is disposed in the groove of the base and the groove of the member to connect the member and the fastener, the crown being stationary relative to the member as the spinal construct moves from the first orientation to the second orientation; wherein the part directly engages the crown when the spinal construct is in the first orientation and the second orientation.

2. A spinal construct as recited in claim 1, wherein the body extends along a longitudinal axis from the top wall to the bottom wall, the crown being stationary along the longitudinal axis as the spinal construct moves from the first orientation to the second orientation.

3. A spinal construct as recited in claim 1, wherein the rod is monolithically formed with the body.

4. A spinal construct as recited in claim 1, wherein the rod is integrally assembled with the member.

5. A spinal construct as recited in claim 1, wherein the crown is spaced apart from the head when the spinal construct is in the first orientation and the crown directly engages the head when the spinal construct is in the second orientation.

6. A spinal construct as recited in claim 1, wherein at the rod includes a first portion connected directly to the side wall, a second portion extending parallel to the first portion and a third portion connecting the first portion and the second portion, the third portion extending non-parallel relative to the first and second portions.

7. A spinal construct as recited in claim 1, further comprising at least one bone fastener defining an implant cavity configured for disposal of the rod.

8. A spinal construct as recited in claim 1, wherein the groove of the base is an outer groove extending into an outer surface of the base.

9. A spinal construct as recited in claim 1, wherein the band is a circumferential ring defining a gap.

10. A spinal construct as recited in claim 1, wherein the head comprises a plurality of ridges, the head being continuously curved from a distalmost one of the ridges to the shaft 360 degrees about the head.

11. A spinal construct as recited in claim 1, wherein the fastener is fixed with the member when the spinal construct is in the second orientation.

12. A spinal construct as recited in claim 1, wherein the base comprises a body and a flange extending from the body, the flange being spaced apart from the member when the spinal construct is in the first orientation, the flange directly engaging the member when the spinal construct is in the second orientation.

13. A spinal construct as recited in claim 1, wherein the groove of the part comprises spaced apart ramps and an intermediate surface disposed between the ramps.

14. A spinal construct as recited in claim 1, wherein the part slides along the crown as the spinal construct moves from the first orientation to the second orientation.

15. A spinal construct as recited in claim 1, wherein the base has a maximum diameter greater than a maximum diameter of the cavity.

16. A spinal construct as recited in claim 1, further comprising a coupling member positioned in the bore such that the coupling member is spaced apart from the rod when the coupling member is fully threaded into the bore.

17. A spinal construct as recited in claim 1, wherein the base includes opposite proximal and distal surfaces and a vertical wall extending continuously from the proximal surface to the distal surface, the vertical wall being free of any openings extending through opposite inner and outer surfaces of the vertical wall.

18. A spinal construct comprising:
- a bone screw comprising a head and a shaft connected to the head, the bone screw including a monolithic base, the head being disposed in the base such that the base extends 360 degrees about the head, the base including a groove;
- a receiver comprising a body having opposite top and bottom walls and a side wall extending from the top wall to the bottom wall, the receiver defining a circular bore extending through the top wall, the body including an inner surface defining an opening extending through the bottom wall, a cavity for disposal of the head and a groove;
- an expandable ring being disposable with the groove of the receiver;
- a transverse rod extending from the side wall such that the rod is permanently fixed to the body;
- a crown disposable in the cavity; and
- a sleeve positioned within the cavity and including a groove,
- wherein the base is configured to move relative to the receiver to move the spinal construct from a first orientation in which the ring is disposed in the groove of the sleeve and the groove of the receiver to a second orientation in which the ring is disposed in the groove of the base and the groove of the receiver to connect the receiver and the bone screw, the crown being stationary relative to the receiver as the spinal construct moves from the first orientation to the second orientation; wherein the sleeve directly engages the crown when the spinal construct is in the first orientation and the second orientation.

19. A spinal construct as recited in claim 18, further comprising at least one bone fastener defining an implant cavity configured for disposal of the rod.

20. A spinal construct comprising:
- a fastener comprising a head and a shaft connected to the head, the fastener including a monolithic base, the head being disposed in the base such that the base extends 360 degrees about the head, the base including a groove;
- a receiver comprising a body having opposite top and bottom walls and a side wall extending from the top wall to the bottom wall, the receiver defining a threaded circular bore extending through the top wall, the body defining a beveled opening extending through the bottom wall, a cavity configured for disposal of the head and a groove configured for disposal of a band, the receiver further including a transverse rod extending from the side wall, the rod being monolithically formed with the body; and
- a part disposed with the cavity and comprising a groove
- the base being configured to move relative to the receiver to move the spinal construct from a first orientation in which the band is disposed in the groove of the part and the groove of the receiver to a second orientation in which the band is disposed in the groove of the base and the groove of the receiver to connect the receiver and the fastener, the crown being stationary relative to the receiver as the spinal construct moves from the first orientation to the second orientation; wherein the part directly engages the crown when the spinal construct is in the first orientation and the second orientation.

* * * * *